(12) United States Patent
Bellar

(10) Patent No.: US 10,395,329 B2
(45) Date of Patent: Aug. 27, 2019

(54) METHOD FOR DEVELOPING INDIVIDUALIZED ATHLETIC TRAINING PROGRAM

(71) Applicant: University of Louisiana at Lafayette, Lafayette, LA (US)

(72) Inventor: David Bellar, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 34 days.

(21) Appl. No.: 14/851,085

(22) Filed: Sep. 11, 2015

(65) Prior Publication Data

US 2016/0184636 A1 Jun. 30, 2016

Related U.S. Application Data

(60) Provisional application No. 62/049,565, filed on Sep. 12, 2014.

(51) Int. Cl.
*G16H 20/30* (2018.01)
*G06Q 50/22* (2018.01)
*G06F 19/00* (2018.01)

(52) U.S. Cl.
CPC ......... *G06Q 50/22* (2013.01); *G06F 19/3481* (2013.01)

(58) Field of Classification Search
CPC ............................ G06Q 50/22; G06F 19/3481
USPC ........................................................ 434/427
See application file for complete search history.

(56) References Cited

U.S. PATENT DOCUMENTS

| | | | | |
|---|---|---|---|---|
| 6,176,241 B1* | 1/2001 | Blau | ............... | A61B 5/222 |
| | | | | 128/898 |
| 2004/0186390 A1* | 9/2004 | Ross | ............... | A61B 5/083 |
| | | | | 600/532 |
| 2010/0286534 A1* | 11/2010 | Greenberg | ...... | A61B 5/0205 |
| | | | | 600/484 |

OTHER PUBLICATIONS

StatSoft, Inc. Software (2013)[online]. Electronic Statistics Textbook. Tulsa, OK: StatSoft. [Retrieved on Jun. 8, 2017]. Retrieved from the internet: http://www.statsoft.com/textbook/; providing PDF "Prior Art StatSoft.pdf"; pp. 1-5.*

Paolo Onorati, et al.; A Simplified Approach for the Estimation of the Ventilatory Compensation Point; Official Journal of the American College of Sports Medicine; Medicine & Science in Sports & Exercise; 2012; pp. 716 through 724.

Paolo Onorati, et al.; Estimation of the Exercise Ventilatory Compensation Point by the Analysis of the Relationship Between Minute Ventilation and Heart Rate; Eur J. Appl. Physiol; May 15, 2008; pp. 1 through 8.

(Continued)

*Primary Examiner* — Robert P Bullington
(74) *Attorney, Agent, or Firm* — Russel O. Primeaux; Jessica C. Engler; Kean Miller LLP

(57) ABSTRACT

The ability to use data from tests of maximum aerobic capacity to determine the ventilatory threshold and point of respiratory compensation (RCP) is useful for coaches, athletes, and other disciplines in the development of training schemes. Current methods for determining the RCP generally involve identifying deflections in respiratory variables when examined along minute ventilation. The present disclosure describes a novel method for crafting training programs by determining the RCP using standard scores (Z scores) for minute ventilation and oxygen consumption. This method offers further benefits as it is not reliant on visual determination of changes in slope of variables of (Continued)

interest, which can often lead to inaccuracy due to human error.

4 Claims, 2 Drawing Sheets

(56) References Cited

OTHER PUBLICATIONS

Daniel G. Carey, et al.; The Ventilatory Response to Incremental Exercise: Is It One or Two Breakpoints?; The Journal of Strenth and Conditioning Research; vol. 24, No. 10; Oct. 2010; pp. 2840 through 2845.
A Lucia, et al.; Which Laboratory Variable Is Related With Time Trial Performance Time in the Tour De France?; British Journal of Sports Medicine; 2004; 38: pp. 636 through 640.

* cited by examiner

METHOD FOR DEVELOPING INDIVIDUALIZED ATHLETIC TRAINING PROGRAM

This application claims the benefit of U.S. Provisional Patent Application No. 62/049,565 filed on Sep. 12, 2014. The disclosures of the referenced application are hereby incorporated herein in its entirety by reference.

The present invention relates to the field of developing individualized exercise training programs, particularly the use of the invention to create polarized training to increase athletic performance.

The development of modern endurance training programs can be optimized by the information derived from tests of maximum aerobic capacity. One such training program, called polarized training, involves training athletes in a variety of different intensities that are based upon defined criteria, such as ventilatory or lactate thresholds. Polarized training, also called "High-Low" training, is a recognized training method that is supported by retrospective training analyses of elite athletes. These elite athletes that use polarized training spend approximately 75 percent of their training time performing low intensity training and approximately 10-15 percent of their training time performing high intensity training.

It has been reported that polarized training schemes can offer significant benefits to both highly trained and recreational athletes in comparison to training based upon more static intensities. Polarized training schemes, and other similar forms of training, require that the athlete to have information about the athlete's anaerobic threshold (AT), which identifies the onset of aerobic to anaerobic metabolic transition, in order to determine the appropriate training intensity level. Most polarized training schemes are centered on the knowledge of both the AT and the point of respiratory compensation (RCP). The RCP is an important concept in developing training programs because the RCP forms the boundary between the heavy and severe exercise intensity domains. It has been suggested that the maintenance of sufficient stimulus of high intensity training is necessary for optimal endurance performance. Based on this information, it is evident that specific mechanisms used to identify the AT and RCP can be useful to endurance athletes and their trainers in developing training schemes that will optimize performance The AT and RCP vary from person to person, and within a given individual, from sport to sport. The RCP has historically been identified using a variety of mechanisms. These methods include comparing minute ventilation (VE) to expired carbon dioxide ($VCO_2$), comparisons of VE to heart rate (HR), the D-max method to define blood lactate kinetics, and examination of the ventilatory equivalents of oxygen ($VE/VO_2$) and carbon dioxide ($VE/VCO_2$) against partial pressure of end tidal carbon dioxide ($PetCO_2$). While these techniques have been reported in the literature to be valid measures, the identification methodology involves the visual determination of slope changes in the variables of interest. This form of identification is a highly subjective form of data interpretation. In addition, visual identification of trends in data introduces the potential for human error in the identifications.

Research has suggested that there are two ventilatory breakpoints in incremental exercise. Based on this evidence, it is important to determine how to best describe these two points. The lower breakpoint, the VT, has received extensive attention in the research literature. The upper breakpoint, the RCP, has received some attention, however, a variety of methods still are in use that rely on visual identification of exponential increases in equivalents of oxygen and carbon dioxide.

To properly develop training programs in endurance athletes, it is important to be able to objectively identify training intensities that are appropriate based on the AT and the RCP, especially if the training program is to be polarized. Given that the RCP generally determines the point where an athlete will advance from rigorous to extremely taxing exercise, it is valuable for the athlete to have knowledge of how this can be determined to adjust additional training plans. While there are several methods for determining the AT, few methods exist for quantification of the RCP. The existing methods for RCP determination suffer further because they are reliant upon visual inspection of the data, which can introduce unwanted variability and error. A novel method for determining the RCP is disclosed and claimed herein, which uses the score transformation of VE and $VO_2$ data, based upon a calculated point of intersection between two regression lines and relates this to real world performance measures.

SUMMARY OF THE INVENTION

A novel method for determination of the RCP, which is then used to create a training plan, is disclosed. In order to perform this method, the athlete's height and mass are first determined. Then the athlete undergoes a number of exercise tests while using a metabolic measurement system that can sample and analyze the air expired by the athlete. The athlete's heart rate is also measured during the exercise tests. For each incremental test, the intensity of the exercise is steadily increased until the conclusion of the tests. For the test, $VO_2$ max is determined based upon a plateau in oxygen consumption, a respiratory exchange ratio of >1.15, and attainment of a heart rate within 10 beats per minute of the documented age-predicted maximum. In the preferred embodiment, the exercise performed during the test is done through a graded exercise test.

After the athlete's $VO_2$ and VE are collected from the test, the RCP is then determined. First, the $VO_2$ and VE data is converted into standard (Z) scores, preferably using a statistical software package (SPSS) for each independent exercise tests. The Z scores for $VO_2$ and VE are then plotted against time and a curve fitting module used to create regression lines for each variable. Next, the point where these two regression lines intersect is calculated and identified as the time during the test when the VE became disproportionately elevated as compared to oxygen consumption. Last, this time is evaluated against the raw test data to determine the oxygen consumption and heart rate at RCP for the athlete. The athlete then uses the RCP to craft an endurance training plan in which heavy intensity exercise is performed between the AT and RCP.

The present method is a reliable improvement of previously known methods. Statistical analyses were performed in order to confirm the accuracy of this method. For illustrative purposes, the method was tested using participants drawn from a pool of runners from a local 10K race, which included a wide range of fitness levels. By way of illustration, to demonstrate the validity of the method, the results were compared to results obtained from methods already known in the art.

In performing statistical analysis of the result using the novel method and methods known in the art, the data was analyzed for normality via Shapiro-Wilks tests. Pearson's correlations were used to compare the relationship between the novel Z-score method for RCP, a previously described method to determine RCP and the V-Slope method to determine VT. Anova analysis was used to assess difference in oxygen consumption identified by each technique. Multiple linear regression analyses (predictors: athletic classification, body mass and absolute oxygen consumption at RCP) were used to determine the relationship of the Z-score method for RCP determination, and previously described methods for RCP determination to 10K race performance.

The data suggests that the point identified by the method was associated with a previously established method of RCP determination and beyond the VT observed during a graded exercise test. Moreover, the ability of the method to produce a chart where the key concept of RCP may be readily observed, namely that the VE is disproportionally elevated as compared to $VO_2$ afterwards, attests to the validity of the measure. The method further produces results that can be associated with real world performance including race performance and other athletic performance. Last, the Z-score method for determining RCP as disclosed herein relies on the applications of mathematics to solve for a point of intersection between two regression lines, thereby eliminating the need to have visual examination of data trends.

The Z-score method results in stronger prediction of race performance when entered into a similar regression model as did the previous RCP method. In the testing example disclosed above, Z-score RCP regression model was able to predict 82.4% of the variance in mean race speed as compared to only 69.9% for the previous RCP method. Given that this Z-score method is not subject to the introduction of error via visual inspection of the data, the Z-score method is more predictive of performance.

A person having ordinary skill in the art will recognize that these disclosed methods can have other applications. For example, the disclosed method allows for students in Exercise Science or Exercise Physiology course work to have a visual representation of the RCP. Other methods do not result in a clear cross-over between two data lines that identifies a point of hyperventilation during exercise. The use of this algorithm in university courses can enrich the experience of the students, and offer clarity on a concept that is often depicted in a more abstract form. Given that a carbon dioxide sensor in not required for this technique, many high school biology classes will have equipment to use this algorithm to demonstrate physiological functions in the respiratory and cardiovascular systems.

DETAILED DESCRIPTION OF THE INVENTION

Figure 1:
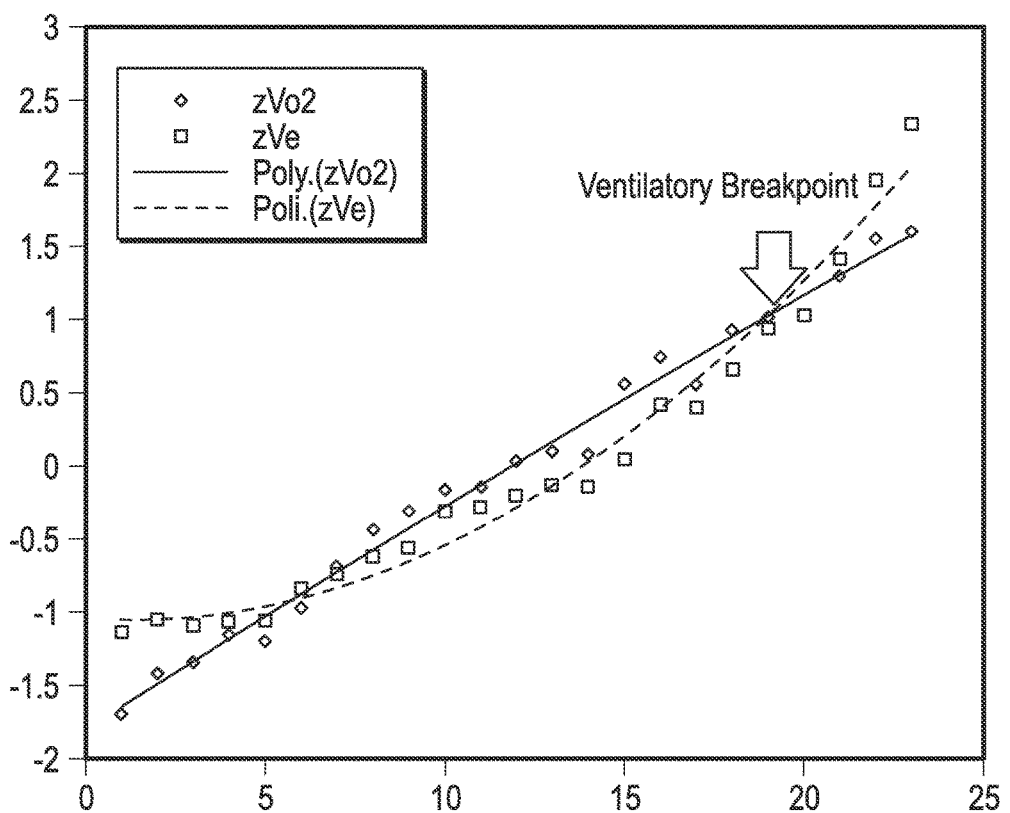
FIG. 1 depicts an example of standard score interpretation of the RCP for one athlete. The X-axis data points represent 20 seconds of mean data from a test of maximum aerobic capacity exercise leading up to the RCP. VE and $VO_2$ are presented as Z-scores with third order polynomial lines of best fit.
Figure 2:
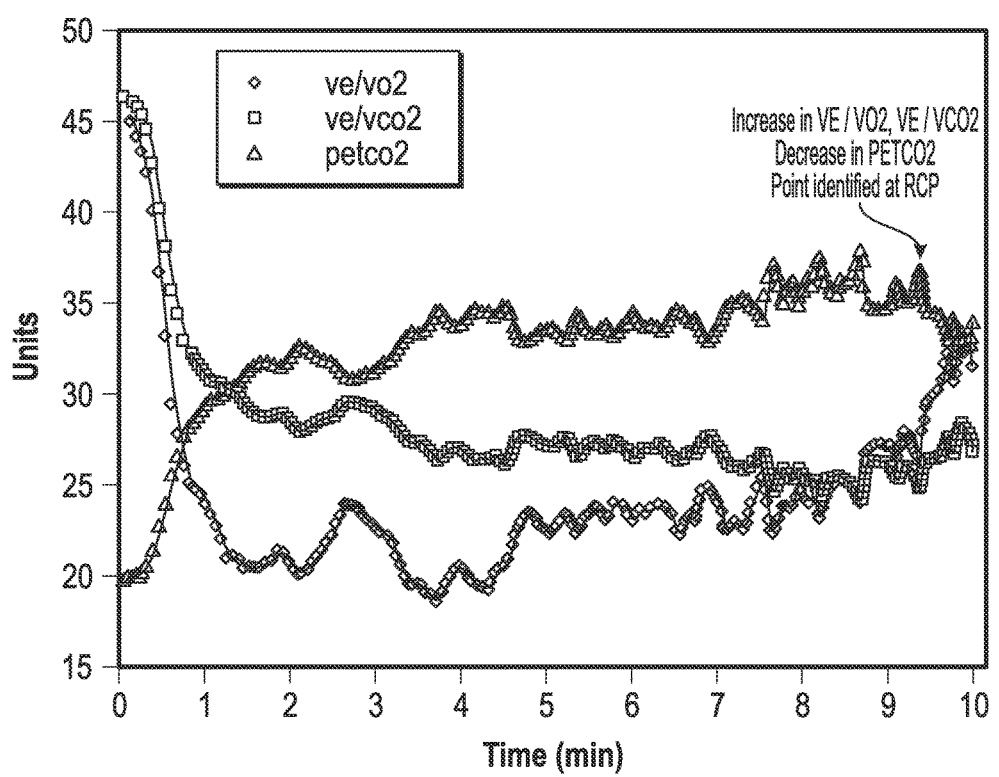
FIG. 2 depicts an example of RCP determination for one athlete by examining the ventilatory equivalents of oxygen ($VE/VO_2$) and carbon dioxide ($VE/VCO_2$) against partial pressure of end tidal carbon dioxide ($PetCO_2$).

The invention disclosed herein presents a novel method for developing a training program for endurance athletes using RCP determination and standard score transformation of VE and $VO_2$ data.

In the preferred embodiment, the athlete's height and mass are first determined using a triple beam balance with a stadiometer attachment. The balance is first checked for proper calibration. Next, the athlete's mass is captured by manipulating the masses on the balance. The athlete is then positioned facing away from the stadiometer and instructed to stand erect with the heel of the feet together and the toes pointed slightly outward. Once alignment with the stadiometer was checked, the athlete is instructed to take a deep breath and hold the breath by standing erect. Once the participant is in the proper position, the arm of the stadiometer is lowered to rest on the crown of the head and a height reading is determined. Additional embodiments may consider other means of measuring height and mass.

The athlete's $VO_2$ is then determined via graded exercise training. In one embodiment, the athlete runs on a TRACK-MASTER® TMX 425 treadmill during the test. The athlete's expired air is sampled and analyzed using a metabolic measurement system. An exemplary metabolic measurement system would be the Parvo Medics™ TrueOne™ 2400. In the preferred embodiment, the metabolic measuring system uses a mixing chamber and is set to sample expired air in regular intervals. The preferred embodiment captures air samples every 20 seconds.

In the preferred embodiment, a validated custom ramp protocol was set on the treadmill. The protocol uses a 30 section initial familiarization stage at a pre-determined speed and grade, and then a two-minute first stage at another predetermined speed and grade. After the initial stage, the speed and grade are routinely increased until the conclusion of the test. Heart rate is measured using a heart rate sensor. Using the heart rate monitor and metabolic measurement system, the $VO_2$ maximum was determined based upon a plateau in oxygen consumption (less than 100 milliliter oxygen change with increased workload), a respiratory exchange ratio of greater than 1.15, and attainment of a heart rate within 10 beats per minute of the athlete's age-predicted maximum.

Next, the V-Slope VT is determined so that the RCP could be verified to occur at a point of higher oxygen consumption than the ventilator threshold. A person having ordinary skill in the art will recognize that various methods exist in the art to determine the VT.

The athlete's $VO_2$ (L $O_2$/minute) and VE (L/minute) is collected from the graded exercise test. Using this data, the $VO_2$ and VE data is converted to standard, or "Z", scores using a known statistical software package (SPSS) for each independent exercise test. The data points are then plotted against time, and a curve-fitting module is used to fit the data to the graph for both $VO_2$ and VE. The point where the two regression lines intersect is calculated, giving the time during the test when VE became disproportionally elevated as compared to oxygen consumption. Then, the time is evaluated against the raw tests data to determine the oxygen consumption at RCP for each individual.

Using either a set pace or a beats per minute measurement, the athlete then develops an endurance training plan in which the high intensity workouts will performed between the AT and the RCP.

In additional embodiments, the method described herein can be used for physical therapy and weight loss patients to prescribe an exercise program to promote healing or weight loss.

In an additional embodiment, the RCP is recalculated at regular intervals over the course of an athlete's training program in order to recalibrate the RCP according to changes in the athlete's mass or body composition.

I claim:

1. A method for enhancing an individualized athletic training program comprising the following steps:
   (a) measuring a height and a mass of at least one athlete; at least one athlete performs a graded exercise test;
   (b) a metabolic measurement system collects oxygen consumption data and minute ventilation data for the at least one athlete during the graded exercise test; wherein the metabolic measurement system comprises a mixing chamber; wherein the metabolic measurement system samples air expired by the at least one athlete at regular intervals;
   (c) converting the oxygen consumption data and minute ventilation data to standard (Z) scores;
   (d) plotting a data time and a curve fitting module to show one regression line for the oxygen consumption data and one regression line for the minute ventilation data;
   (e) calculating a point where said regression lines intersect;
   (f) evaluating time against the data to determine a point of respiratory compensation;
   (g) identifying an onset of aerobic to anaerobic metabolic transition for the at least one athlete; and
   (h) preparing an athletic training plan for the at least one athlete using the point of respiratory compensation, wherein at least one exercise is performed between the onset of aerobic to anaerobic metabolic transition and the point of respiratory compensation of the at least one athlete, and wherein the point of respiratory compensation is recalculated to address one or more changes in the at least one athlete's mass.

2. The method as claimed in claim 1 wherein the oxygen consumption data and the minute ventilation data are converted using a statistical software package.

3. The method as claimed in claim 1, wherein the at least one athlete runs on a treadmill during the graded exercise test.

4. The method as claimed in claim 3, wherein the treadmill comprises a validated custom ramp protocol.

* * * * *